United States Patent
Sugita et al.

(10) Patent No.: US 8,100,904 B2
(45) Date of Patent: Jan. 24, 2012

(54) TREATMENT TOOL FOR ENDOSCOPE

(75) Inventors: Noriyuki Sugita, Saitama (JP); Kikuo Iwasaka, Saitama (JP)

(73) Assignee: Hoya Corporation, Tokyo (JP)

( * ) Notice: Subject to any disclaimer, the term of this patent is extended or adjusted under 35 U.S.C. 154(b) by 1119 days.

(21) Appl. No.: 11/930,505

(22) Filed: Oct. 31, 2007

(65) Prior Publication Data
US 2008/0114353 A1    May 15, 2008

(30) Foreign Application Priority Data
Nov. 9, 2006   (JP) .................................. 2006-303435

(51) Int. Cl.
A61B 18/18    (2006.01)
(52) U.S. Cl. ................ 606/47; 606/48; 606/41
(58) Field of Classification Search .............. 606/41–48
See application file for complete search history.

(56) References Cited

U.S. PATENT DOCUMENTS

| | | | |
|---|---|---|---|
| 6,689,130 B2 * | 2/2004 | Arai et al. ........................ 606/46 |
| 6,802,840 B2 | 10/2004 | Chin et al. | |
| 2002/0087151 A1 | 7/2002 | Mody et al. | |
| 2002/0128636 A1 | 9/2002 | Chin et al. | |
| 2003/0050631 A1 | 3/2003 | Mody et al. | |
| 2004/0064015 A1 | 4/2004 | Goto et al. | |
| 2004/0172018 A1 | 9/2004 | Okada | |
| 2005/0215853 A1 | 9/2005 | Ouchi | |
| 2006/0178656 A1* | 8/2006 | Sugita et al. ...................... 606/1 |
| 2006/0178657 A1 | 8/2006 | Sugita et al. | |
| 2006/0178669 A1* | 8/2006 | Sugita et al. .................... 606/45 |
| 2006/0259043 A1* | 11/2006 | Miyamoto et al. ............. 606/139 |
| 2007/0100405 A1* | 5/2007 | Thompson et al. ........... 607/113 |
| 2007/0203487 A1 | 8/2007 | Sugita | |
| 2007/0282336 A1 | 12/2007 | Kawano | |

FOREIGN PATENT DOCUMENTS

| | | |
|---|---|---|
| JP | 5-211994 | 8/1993 |
| JP | 2004-57815 | 2/2004 |
| JP | 2004-229947 | 8/2004 |
| JP | 2004-261372 | 9/2004 |
| JP | 2005-137916 | 6/2005 |
| JP | 2005-270240 | 10/2005 |

OTHER PUBLICATIONS

English language Abstract of JP 5-211994.

* cited by examiner

Primary Examiner — Linda Dvorak
Assistant Examiner — Amanda Scott
(74) Attorney, Agent, or Firm — Greenblum & Bernstein P.L.C.

(57) ABSTRACT

A treatment tool for an endoscope includes a flexible sheath, with a transparent portion near a distal end thereof, which is inserted into and ejected from a treatment tool insertion channel of the endoscope, a rod-shaped treatment piece arranged into the flexible sheath, an operation wire arranged inside the flexible sheath with a distal end thereof being connected with the rod-shaped treatment piece such that the rod-shaped treatment piece is projected back and forth from the distal end of the flexible sheath by operating the operation wire, and a mobile indicator formed at the rod-shaped treatment piece or a portion of the operation wire near the distal end thereof to move along with movement of the rod-shaped treatment piece and to be visually recognized through the transparent portion of the flexible sheath from an outside of the flexible sheath.

14 Claims, 14 Drawing Sheets

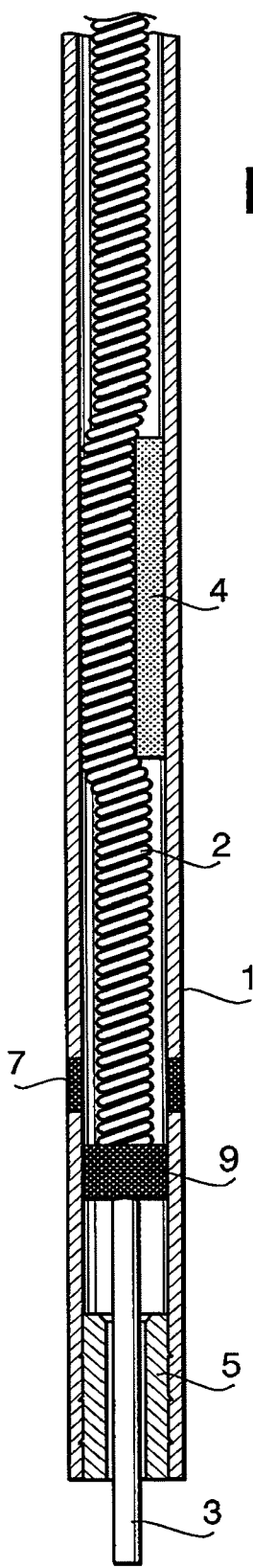
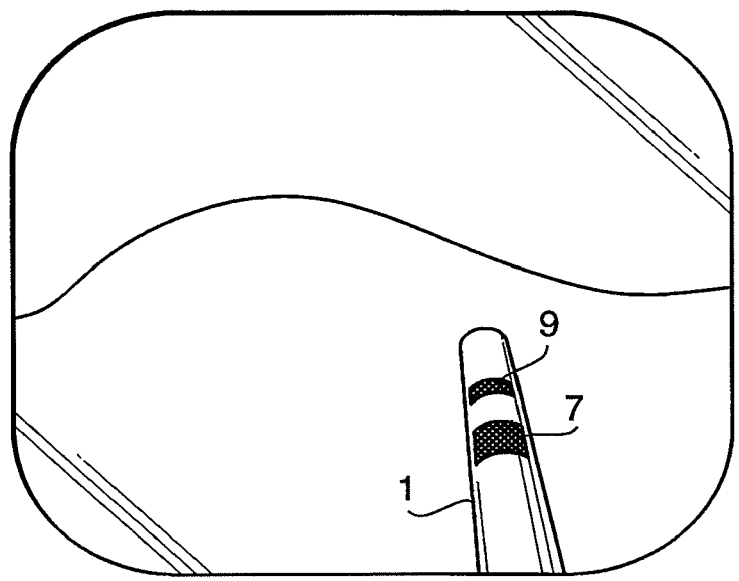
FIG.14
FIG.15

TREATMENT TOOL FOR ENDOSCOPE

BACKGROUND OF THE INVENTION

The present invention relates to a treatment tool for an endoscope.

Among various kinds of treatment tools for an endoscope, there is known a rod-shaped treatment piece such as a high frequency incision tool with a rod-shaped electrode provided to be pulled in and pushed out from a distal end of a flexible sheath. The rod-shaped treatment piece is configured to be ejected forward from (and inserted backward into) the distal end of the flexible sheath by operating an operation wire arranged to be movable back and forth along an axis line thereof in the flexible sheath (for example, U.S. Patent Application Publication No. 2005/0215853).

According to the aforementioned high frequency incision tool for the endoscope, it is required to appropriately adjust a length of a projecting portion of the rod-shaped electrode depending on a state of a biomedical tissue to be incised. To meet the requirement, the rod-shaped electrode is monitored on an observation window so that the length of the projecting portion thereof can be checked.

However, as shown in FIG. 17, when the rod-shaped electrode 92 is viewed from an observation port 91 of the endoscope, the rod-shaped electrode 92 is partially hidden by the flexible sheath 93 with a diameter larger than that of the rod-shaped electrode 92. Namely, as shown in FIG. 18, a part beyond a predetermined projection length of a portion projecting from the distal end of the flexible sheath 93 can only be monitored through the observation port 91 of the endoscope. Consequently, it is impossible to check an accurate length of the portion of the rod-shaped electrode 92 that projects from the distal end of the flexible sheath 93.

In addition, as shown in FIG. 19, in a state where the high frequency incision tool 90 for the endoscope projects from the endoscope by more than a predetermined length, the rod-shaped electrode 92 is completely hidden by the flexible sheath 93. Hence, as shown in FIG. 20, the rod-shaped electrode 92 cannot at all be observed on the observation window of the endoscope, and thereby an endoscopic treatment such as high frequency incision might not safely be implemented.

SUMMARY OF THE INVENTION

The present invention is advantageous in that there can be provided an improved treatment tool for an endoscope that makes it possible to visually check an accurate length of a portion of a rod-shaped treatment piece that projects from a distal end of a flexible sheath and to constantly perform a secure endoscopic treatment.

According to an aspect of the present invention, there is provided a treatment tool for an endoscope, which includes a flexible sheath configured to be inserted into and ejected from a treatment tool insertion channel of the endoscope, the flexible sheath including a transparent portion near a distal end thereof, a rod-shaped treatment piece arranged into the flexible sheath, an operation wire arranged inside the flexible sheath to move back and forth along an axis line of the flexible sheath, a distal end of the operation wire being connected with the rod-shaped treatment piece such that the rod-shaped treatment piece is projected back and forth from the distal end of the flexible sheath by operating the operation wire, and a mobile indicator formed at one of the rod-shaped treatment piece and a portion of the operation wire near the distal end thereof so as to move along with movement of the rod-shaped treatment piece, the mobile indicator being visually recognized through the transparent portion of the flexible sheath from an outside of the flexible sheath.

Optionally, the rod-shaped treatment piece may include a high frequency electrode. In this case, the flexible sheath may be formed from an electrical insulating tube, and the operation wire may have a function of a conductive wire carrying an electrical current to the high frequency electrode.

Still optionally, the operation wire may be formed with a stainless steel thin wire being twined or coil-wound around a core wire connected integrally with the rod-shaped treatment piece.

Optionally, the treatment tool may further include a braking member configured to give frictional resistance against the movement of the operation wire inside the flexible sheath so as to hold the rod-shaped treatment piece in a state projected from the distal end of the flexible sheath by a desired length.

Yet optionally, the braking member may include a flexible tube fitted between the operation wire and an inner circumferential surface of the flexible sheath.

Further optionally, the braking member may be formed from a tetrafluoroethylene resin tube.

Optionally, the treatment tool may further include a tubular distal end tip fitted into the distal end of the flexible sheath, the distal end tip being configured such that the rod-shaped treatment piece passes therethrough.

Optionally, the treatment tool may further include a stopper provided at a base of the rod-shaped treatment piece, the stopper being configured to establish contact with a rear end of the distal end tip so as to regulate a maximum projection length of the rod-shaped treatment piece projecting from the distal end of the flexible sheath.

Still optionally, the mobile indicator may be formed on an outer circumferential surface of the stopper.

Optionally, the treatment tool may further include an immobile indicator formed on an outer circumferential surface of the distal end tip to be visually recognized through the transparent portion of the flexible sheath from the outside of the flexible sheath.

Yet optionally, the immobile indicator may be formed at a rear end on the outer circumferential surface of the distal end tip.

Alternatively or optionally, the immobile indicator may include a plurality of immobile indicators formed on the outer circumferential surface of the distal end tip along an axis line of the rod-shaped treatment piece at intervals of a predetermined distance.

Optionally, the mobile indicator may include a plurality of mobile indicators formed on the outer circumferential surface of the rod-shaped treatment piece along an axis line of the rod-shaped treatment piece at intervals of a predetermined distance.

Still optionally, the distal end tip may be formed to be too opaque to visually recognize ones of the mobile indicators shifted thereinto through the transparent portion of the flexible sheath from the outside of the flexible sheath.

Further optionally, the distal end tip may be formed from electrical insulating polyetheretherketone (PEEK) resin.

Optionally, the immobile indicator may be formed at the flexible sheath to be visually recognized from the outside of the flexible sheath.

Still optionally, the immobile indicator may be formed in such a position at the flexible sheath as to overlap the mobile indicator when a leading edge of the rod-shaped treatment piece conforms with a leading edge of the flexible sheath.

Optionally, the immobile indicator may be formed by one of chemical treatment for the flexible sheath and coating around the flexible sheath.

Alternatively or optionally, the immobile indicator may be formed from a heat shrinkable tube.

Optionally, the flexible sheath may include one of a sheath formed from a transparent flexible tube over an entire length thereof and a sheath formed with a transparent flexible tube being connected with a distal end of an opaque flexible tube.

BRIEF DESCRIPTION OF THE ACCOMPANYING DRAWINGS

Figure 6:
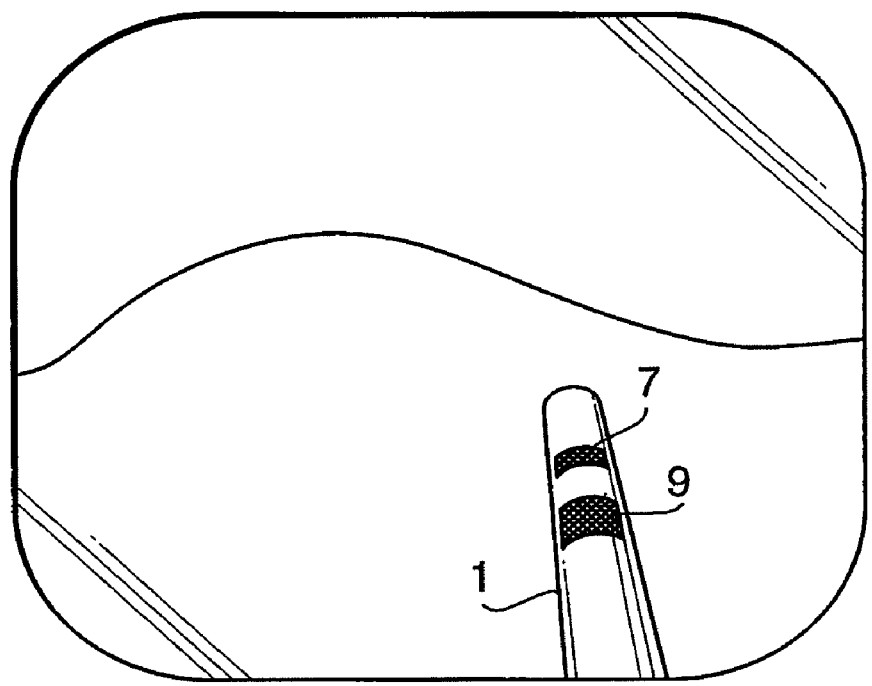

FIG. 6 schematically shows an endoscopic observation image in the first embodiment according to the present invention.

Figure 7:
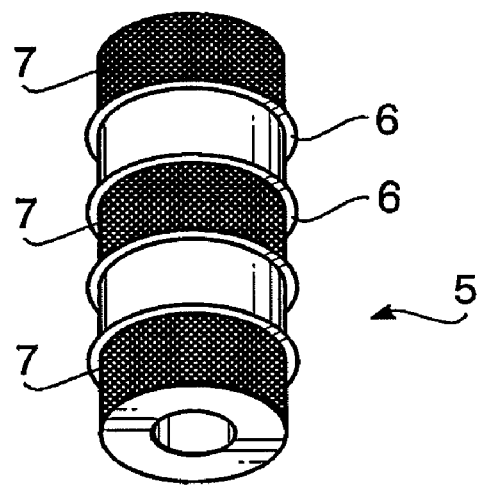

FIG. 7 is a perspective view of a distal end tip of a treatment tool for the endoscope in a second embodiment according to the present invention.

Figure 8:
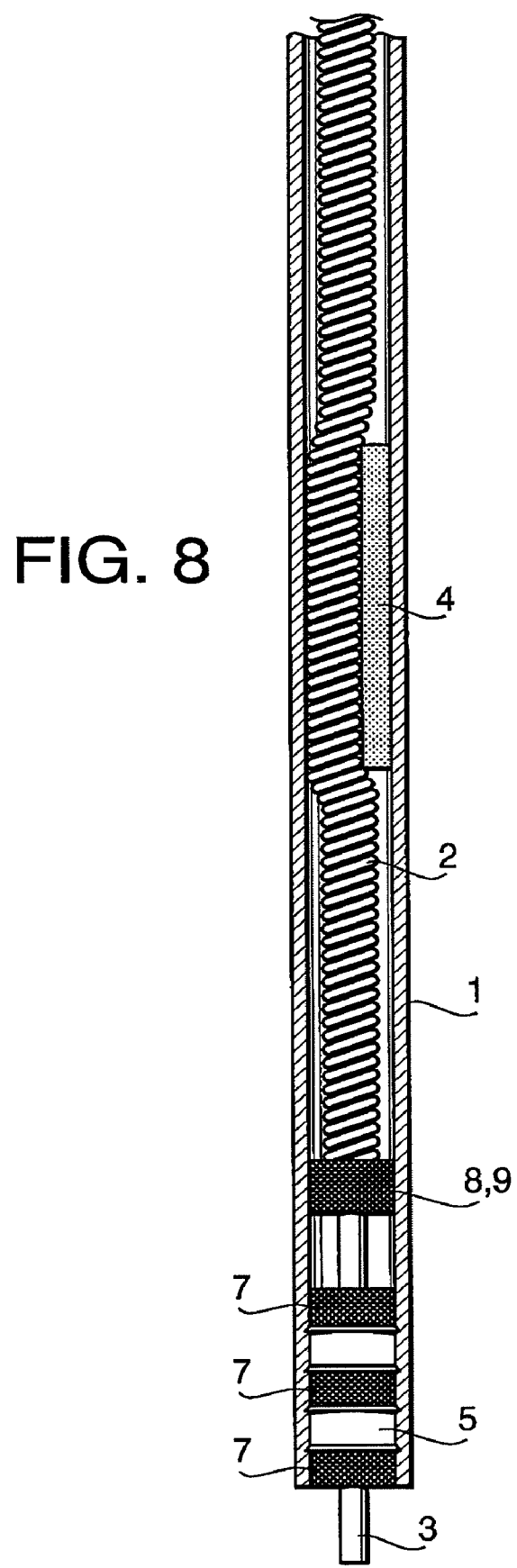
Figure 9:
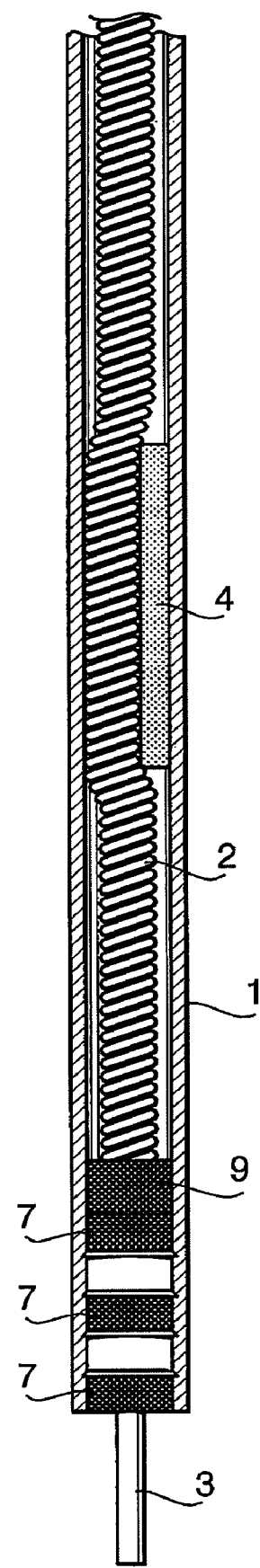

FIGS. 8 and 9 are side views of a distal end portion of the treatment tool for the endoscope in a state where the flexible sheath is only cut off along an axis line of the flexible sheath in the second embodiment according to the present invention.

Figure 10:
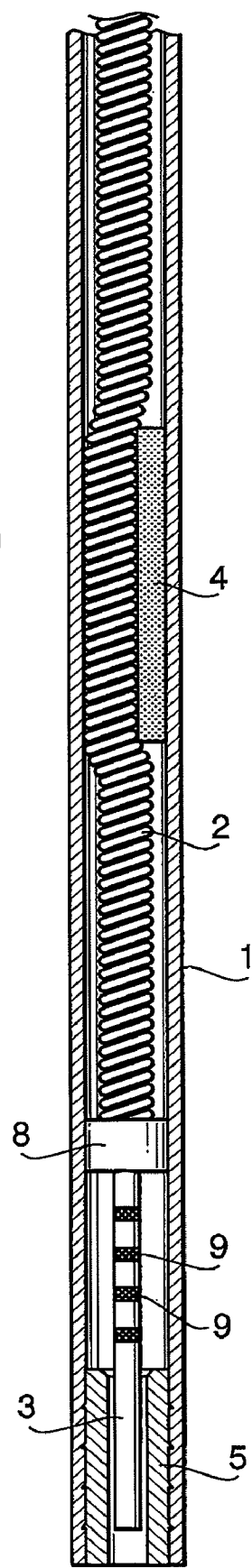
Figure 11:
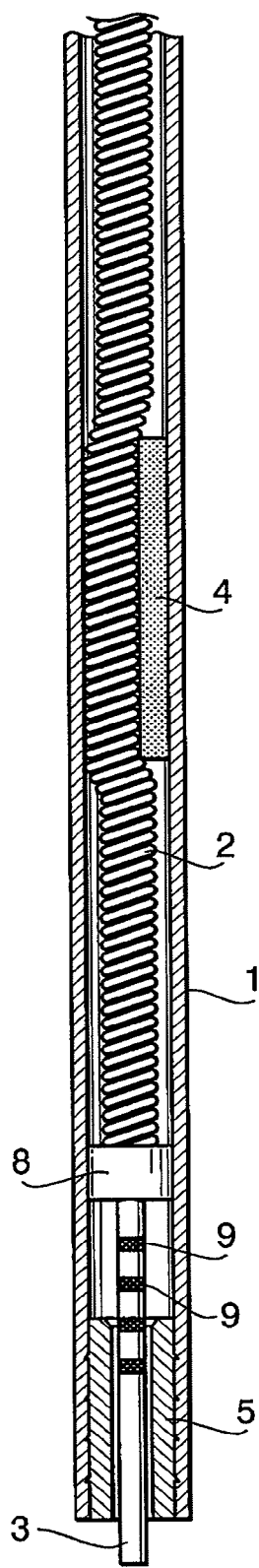

FIGS. 10 and 11 are side views of a distal end portion of a treatment tool for the endoscope in a state where the flexible sheath and a distal end tip are cut off along the axis line in a third embodiment according to the present invention.

Figure 12:
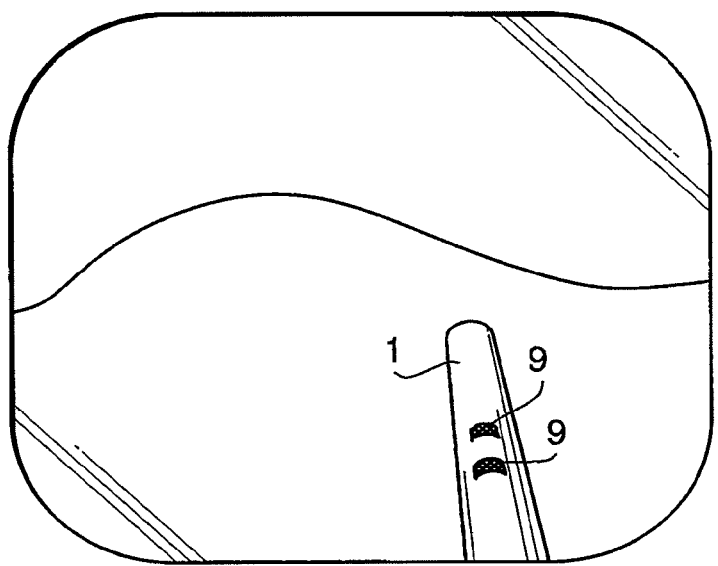

FIG. 12 schematically shows an endoscopic observation image in the third embodiment according to the present invention.

Figure 13:
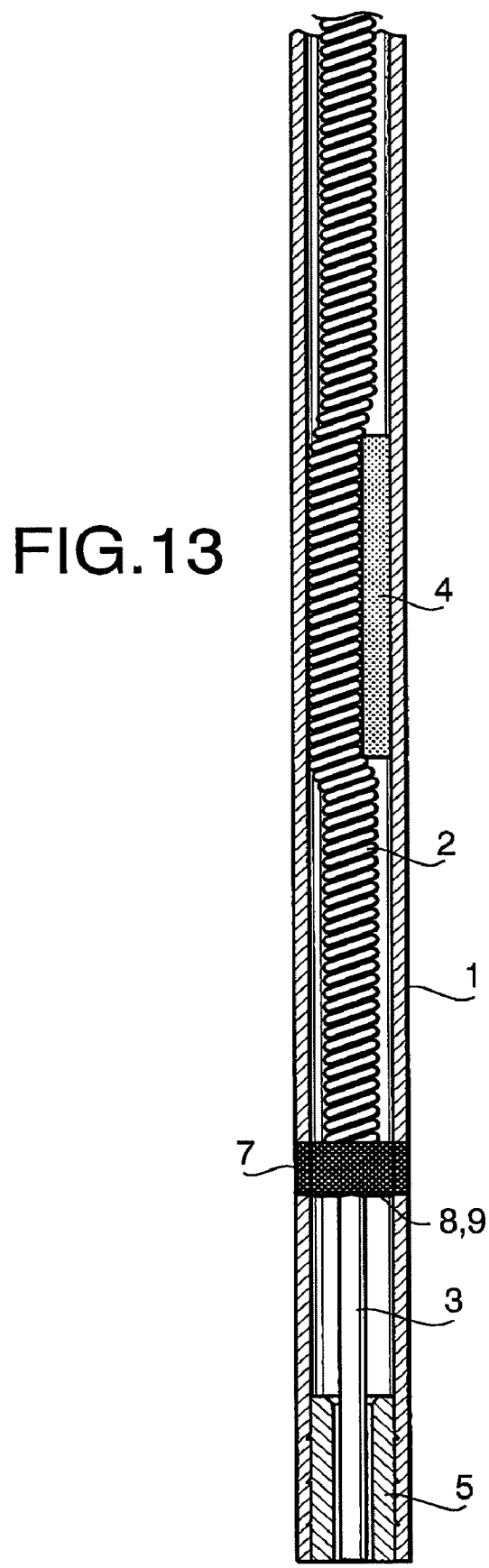

FIGS. 13 and 14 are side views of a distal end portion of a treatment tool for the endoscope in a state where the flexible sheath and distal end tip are cut off along the axis line in a fourth embodiment according to the present invention.

FIG. 15 schematically shows an endoscopic observation image in the fourth embodiment according to the present invention.

Figure 16:
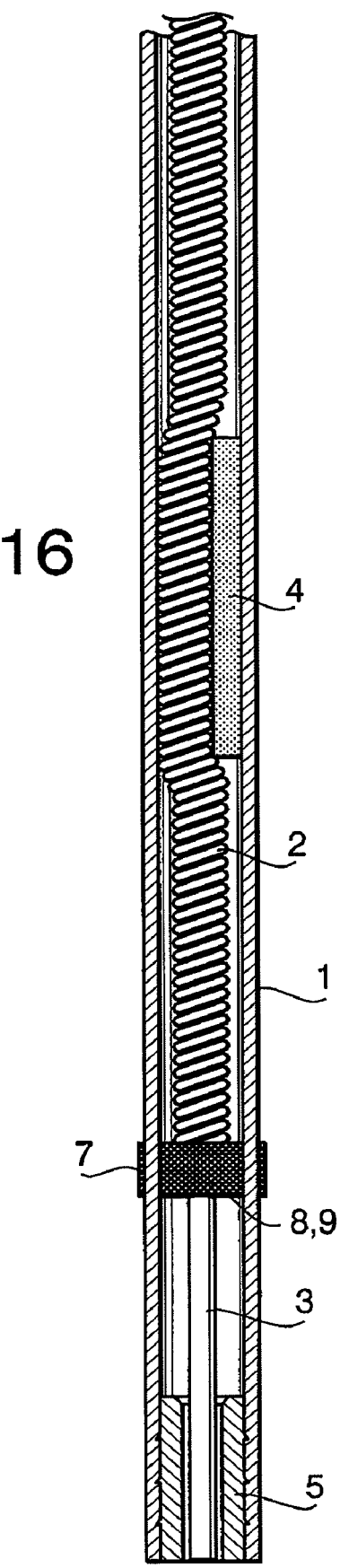

FIG. 16 is a side view of a distal end portion of a treatment tool for the endoscope in a state where the flexible sheath and distal end tip are cut off along the axis line in a fifth embodiment according to the present invention.

Figure 17:
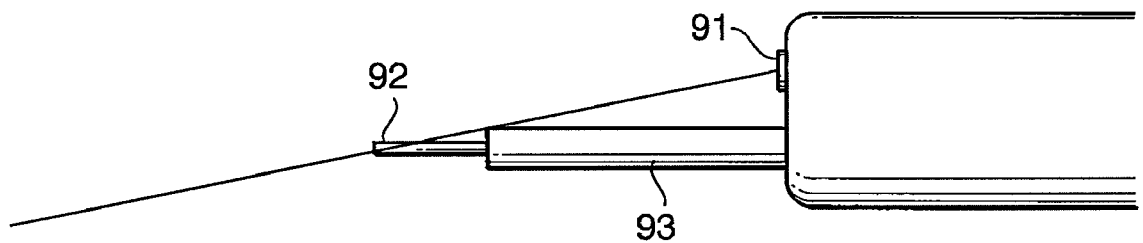

FIG. 17 schematically shows a state where a conventional treatment tool for an endoscope, which is inserted into a treatment tool insertion channel of the endoscope, is used.

Figure 18:
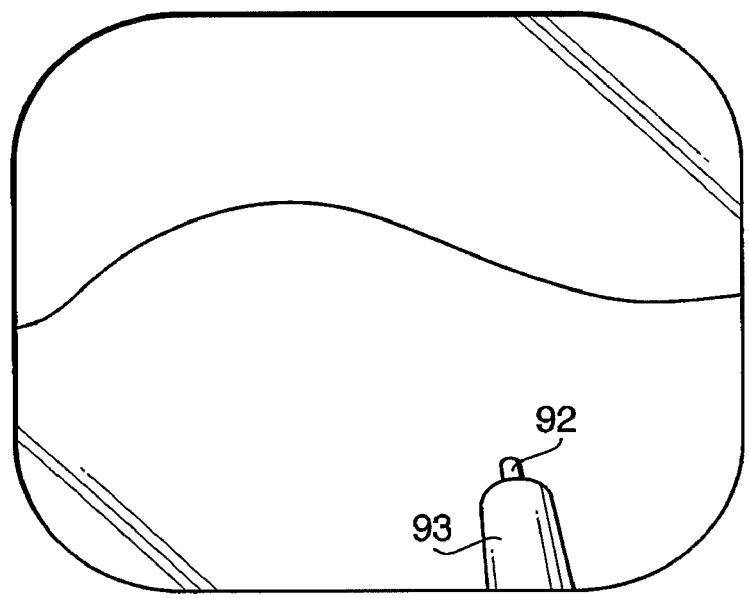

FIG. 18 schematically shows an endoscope observation image of the conventional treatment tool for the endoscope.

Figure 19:
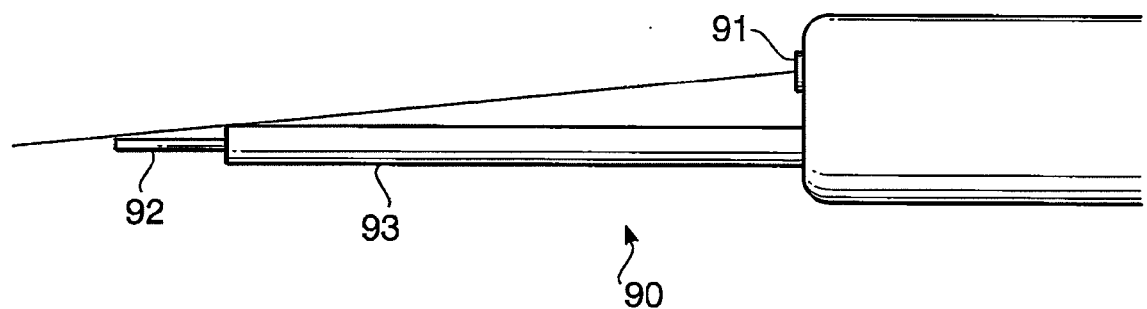

FIG. 19 schematically shows another state where the conventional treatment tool for the endoscope, which is inserted into the treatment tool insertion channel of the endoscope, is used.

Figure 20:
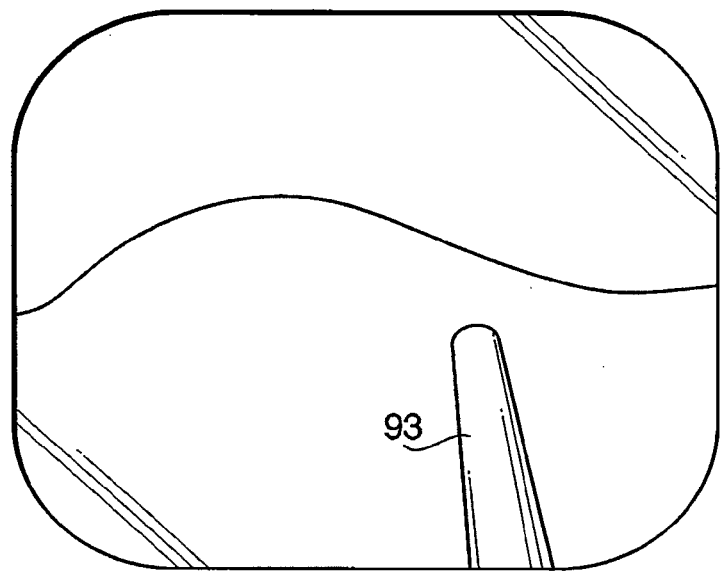

FIG. 20 schematically shows another endoscope observation image of the conventional treatment tool for the endoscope.

DETAILED DESCRIPTION OF THE EMBODIMENTS

Hereinafter, embodiments according to the present invention will be described with reference to the accompanying drawings.

Figure 2:
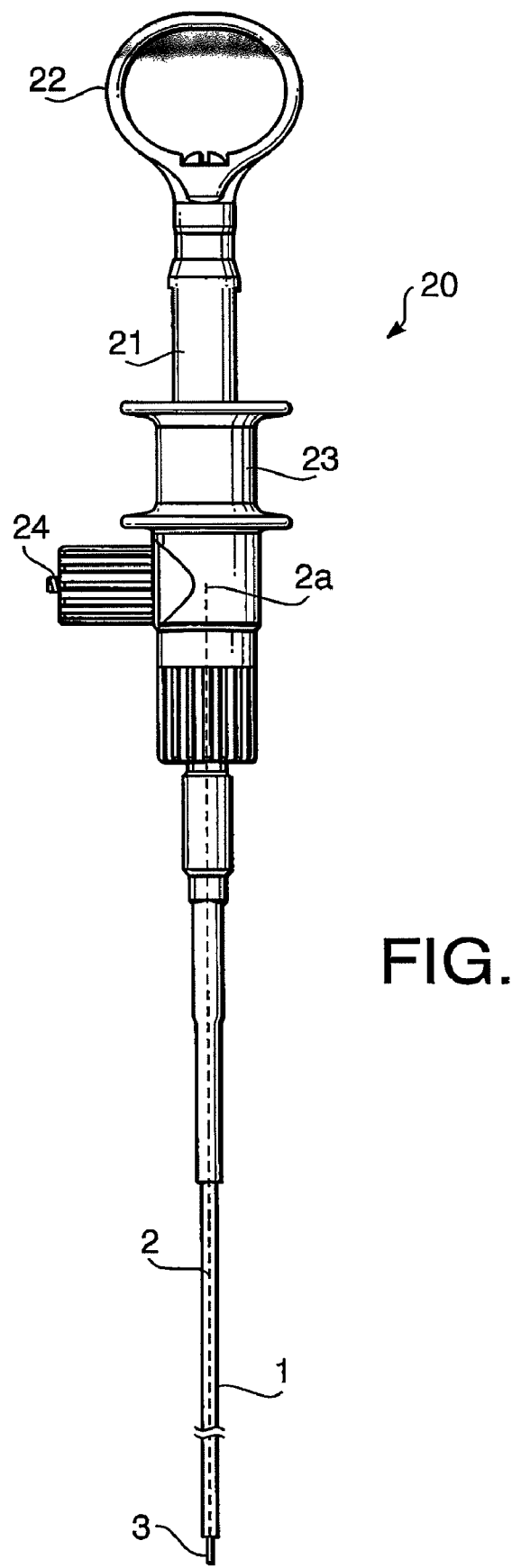
FIG. 2 is a side view showing an entire configuration of the treatment tool for the endoscope in the first embodiment according to the present invention.

FIG. 2 is an entire configuration of a treatment tool for an endoscope in a first embodiment according to the present invention. As shown in FIG. 2, the treatment tool for the endoscope is configured such that an operation wire 2 formed with a conductive wire such as a stainless steel wire being twisted is inserted and arranged in a flexible sheath 1 over an entire length thereof to be movable back and forth with respect to the flexible sheath 1 along an axis line thereof. It is noted that the flexible sheath 1 is formed from a flexible tube such as a tetrafluoroethylene resin tube and configured to be inserted into and ejected from a treatment tool insertion channel (not shown) of the endoscope.

A rod-shaped electrode 3 (rod-shaped treatment piece) as a thin straight conductive high frequency electrode is joined integrally with a distal end of the operation wire 2. Additionally, the rod-shaped electrode 3 is arranged to be ejected forward from (and inserted backward into) the distal end of the flexible sheath 1. The rod-shaped electrode 3 is movable back and forth along an axis line of the flexible sheath 1 with respect to the flexible sheath 1 along with the distal end of the operation wire 2.

What is indicated by a reference number 20 is an operating portion, which includes a fixed finger engaging portion 22 formed at a rear end of an operating portion body 21 linked with a rear anchor of the flexible sheath 1 and a movable finger engaging portion 23 slidably arranged around the operating portion body 21. A rear anchor 2a of the operation wire 2 is linked and fixed to the movable finger engaging portion 23. Further, a connection terminal 24 to be connected with a high frequency power cord (not shown) is placed at the movable finger engaging portion 23 to be electrically connected with the operation wire 2.

Hence, by operating the movable finger engaging portion 23 to slide, the operation wire 2 is shifted along the axis line in the flexible sheath 1, and the rod-shaped electrode 3 is ejected forward (downward in FIG. 2) from the distal end of the flexible sheath 1, so that a projection length of a portion of the rod-shaped electrode 3 that projects from the distal end of the flexible sheath 1 (hereinafter, simply referred to as "projection length") can adequately be adjusted.

Then, by connecting the high frequency power cord to the connection terminal 24, a high frequency electric current is carried to the rod-shaped electrode 3 via the operation wire 2 that also serves as a conductive wire. Thereby, a high frequency treatment can be implemented for a biomedical tissue that is in contact with the rod-shaped electrode 3.

Figure 3:
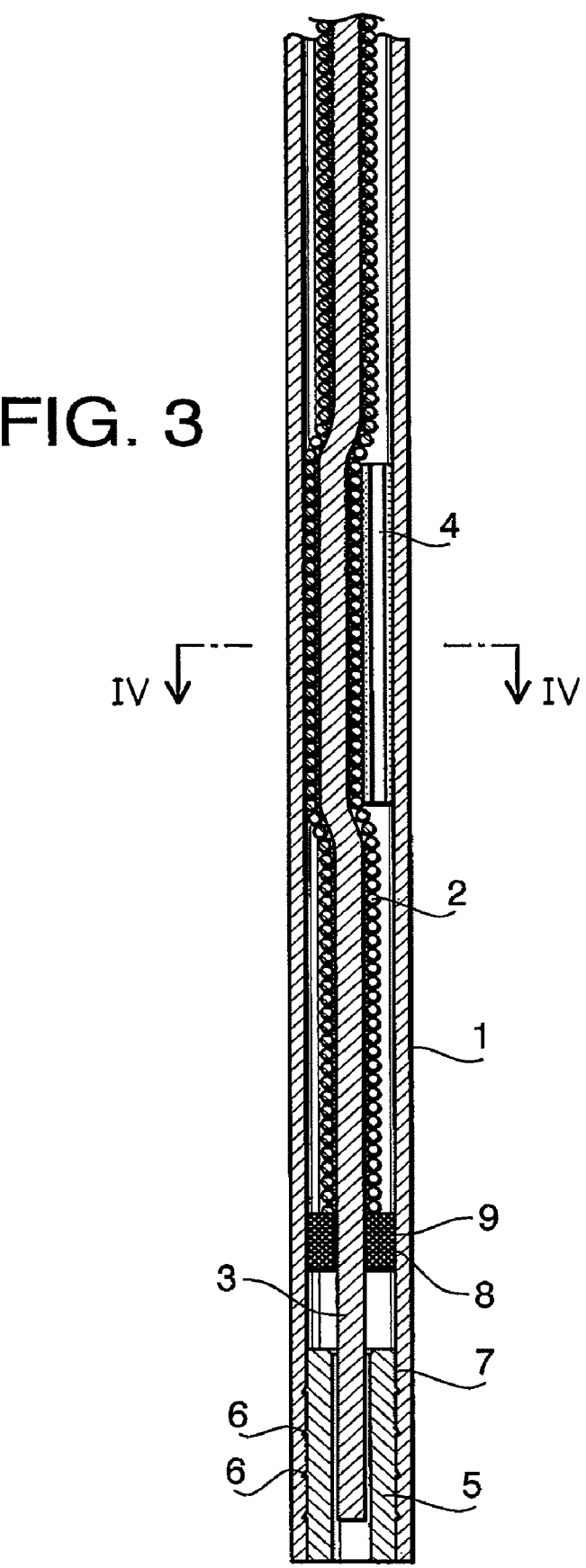
FIG. 3 is a cross-sectional side view of the distal end portion of the treatment tool for the endoscope in the first embodiment according to the present invention.

FIG. 3 shows a distal end portion of the flexible sheath 1. The rod-shaped electrode 3 of the present embodiment is formed with a core wire of the operation wire 2 being extended as it is and configured without a seam between the operation wire 2 and itself.

The operation wire 2 is formed with a stainless steel thin wire being twined or coil-wound around the core wire connected integrally with the rod-shaped electrode 3 as described above. In this regard, however, the operation wire 3 may be provided as an element separate from the rod-shaped electrode 3 and connected with the rod-shaped electrode 3 by a connecting tubule.

As shown in FIG. 3, a soft pressure-contact member 4 is inserted and arranged along the operation wire 2 under pressure in a portion near the distal end of the flexible sheath 1. In the portion near the distal end of the flexible sheath 1, the soft pressure-contact member 4 is contact-pressed by an outer circumferential surface of the operation wire 2 and elastically deformed.

Figure 4:
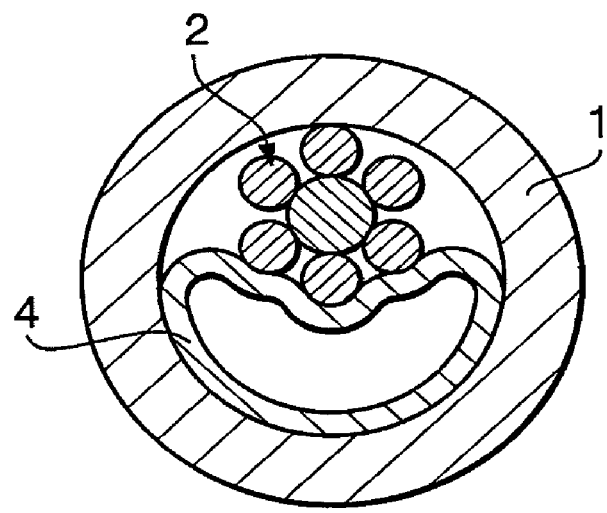
FIG. 4 is a cross-sectional view of the treatment tool for the endoscope along a line IV-IV shown in FIG. 3 in the first embodiment according to the present invention.

The soft pressure-contact member 4 is, for example, a tube member such as a tetrafluoroethylene resin tube with a circular cross-sectional shape. FIG. 4 is a cross-sectional view of the flexible sheath 1 along a line IV-IV shown in FIG. 3. As shown in FIG. 4, the soft pressure-contact member 4 is pressed between an inner circumferential surface of the flexible sheath 1 and the outer circumferential surface of the operation wire 2, and elastically deformed in such a shape that a portion thereof pressed against the operation wire 2 is sunken.

Consequently, the operation wire 2 contacts and engages with the soft pressure-contact member 4 under pressure so that frictional resistance can be generated between the operation wire 2 and the soft pressure-contact member 4. Hence, the operation wire 2 is lightly held in the flexible sheath 1 unless it is operated. Thereby, since the projection length of the rod-shaped electrode 3 is not varied even though the rod-shaped electrode 3 contacts with in vivo mucosa, the rod-shaped electrode 3 can be held in a state projected from the distal end of the flexible sheath 1 by a desired length.

As shown in FIG. 3, a tubular opaque distal end tip 5, which is formed, for example, from electrical insulating polyetheretherketone (PEEK) resin, is inserted into the distal end of the flexible sheath 1 under pressure to be fixed therein. In addition, the rod-shaped electrode 3 is arranged to pass through the distal end tip 5 in a state movable back and forth along an axis line of the distal end tip 5.

Figure 5:
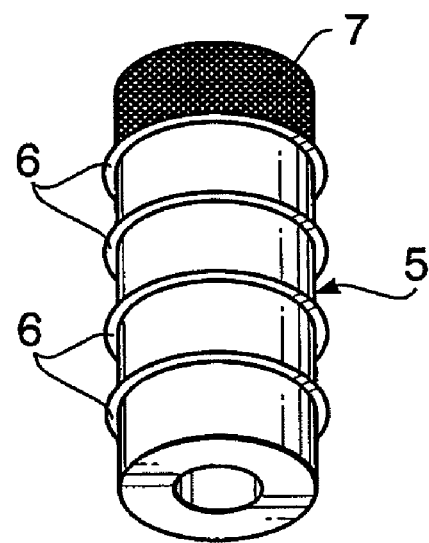
FIG. 5 is a perspective view of a distal end tip of the treatment tool for the endoscope in the first embodiment according to the present invention.

FIG. 5 shows the distal end tip 5 as a single body. As shown in FIG. 5, several small acicular annular projections 6 are formed around an outer circumferential surface of the distal end tip 5. The projections 6 bite into the inner circumferential surface of the flexible sheath 1 and prevent the distal end tip 5 from being pulled out of the flexible sheath 1. There is formed around an entire outer circumference of a rear end portion of the distal end tip 5 an immobile indicator 7 with a color clearly different from the other portions of the distal end tip 5.

Referring back to FIG. 3, there is fixed to a base of the rod-shaped electrode 3 a short-cylindrical stopper 8 that establishes contact with a rear end surface of the distal end tip 5 to regulate the maximum projection length of the rod-shaped electrode 3. The stopper 8 has an outer diameter configured to lightly fit an inner diameter of the flexible sheath 1.

Around an entire outer circumference of the stopper 8, there is formed a mobile indicator 9 with a color clearly different from the other portions of the stopper 8. Hence, the mobile indicator 9 moves inside the flexible sheath 1 along with the movement of the rod-shaped electrode 3 and operation wire 2. It is noted that the respective colors of the mobile indicator 9 and the immobile indicator 7 may be the same or different.

At least distal end portion of the flexible sheath 1, inside which the mobile indicator 9 and immobile indicator 7 are located, is formed from a transparent flexible tube. For example, the flexible sheath 1 may be formed from the transparent flexible tube over an entire length thereof or formed with an opaque flexible tube being joined with the transparent flexible tube. It is noted that a term "transparent" in the present invention means a state where the immobile indicator 7 and the mobile indicator 9 can visually be recognized from the outside of the flexible sheath 1 and includes "half-transparent."

Figure 1:
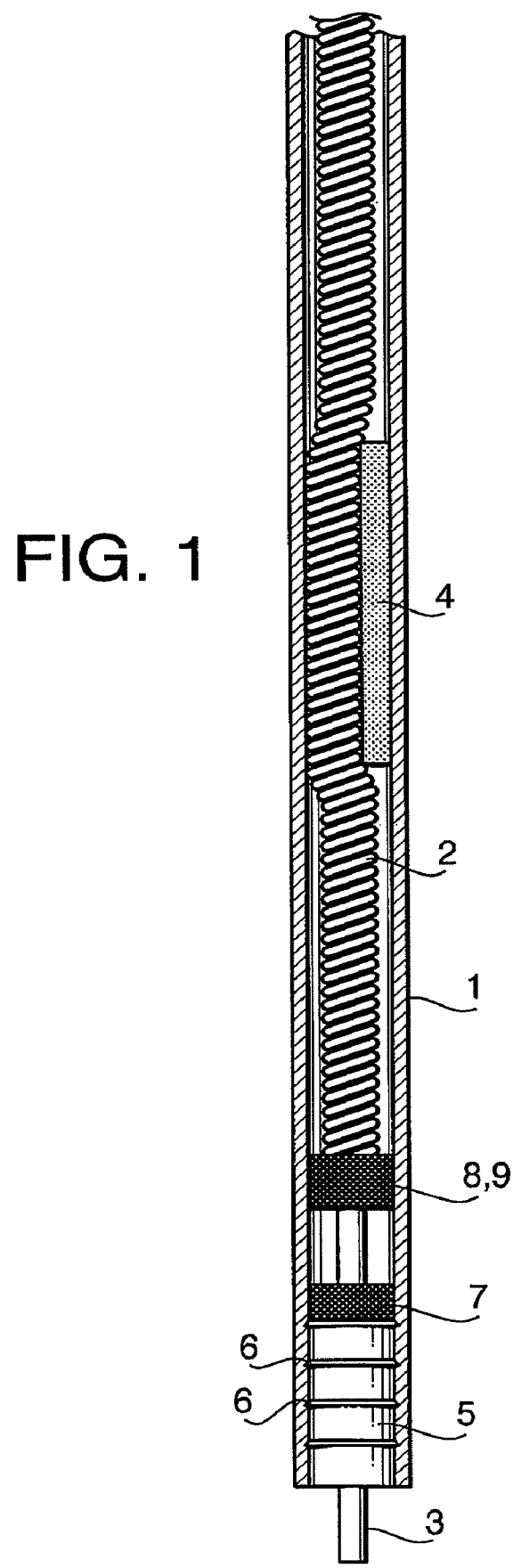
FIG. 1 is a side view of a distal end portion of a treatment tool for an endoscope in a state where a flexible sheath is only cut off in a first embodiment according to the present invention.

According to the treatment tool for the endoscope configured as above, as shown in FIG. 1, the immobile indicator 7 and the mobile indicator 9, formed with the respective colors clearly different from the other portions, can visually be recognized through the transparent flexible sheath 1 from the outside of the flexible sheath 1. A distance between the immobile indicator 7 and the mobile indicator 9 varies depending on the projection length of the rod-shaped electrode 3. In the present embodiment, the distance between the immobile indicator 7 and the mobile indicator 9 is reduced as the projection length of the rod-shaped electrode 3 increases.

Consequently, as shown in FIG. 6, the immobile indicator 7 and the mobile indicator 9 can be observed through the transparent portion of the flexible sheath 1 projected from the distal end of the endoscope on an observation window. Therefore, even though the projecting portion of the rod-shaped electrode 3 is hidden by the flexible sheath 1 (distal end tip 5), the projection length of the rod-shaped electrode 3 can be checked based on the distance between the immobile indicator 7 and the mobile indicator 9. Accordingly, a high frequency treatment can securely be performed by adequately controlling the projection length of the rod-shaped electrode 3.

FIG. 7 shows a distal end tip 5 of a treatment tool for the endoscope in a second embodiment according to the present invention. A plurality of immobile indicators 7 are formed around the outer circumferential surface of the distal end tip 5 at intervals of a predetermined distance. The other constitutions are the same as the first embodiment.

Thereby, as shown in FIGS. 8 and 9, the distance between the mobile indicators 9 and one of the immobile indicators 7 located close the mobile indicators 9 can be checked more easily by comparing it with the distance between each couple of adjacent immobile indicators 7. Accordingly, the projection length of the rod-shaped electrode 3 can be grasped more accurately.

FIG. 10 shows a treatment tool for the endoscope in a third embodiment according to the present invention. As shown in FIG. 10, a plurality of immobile indicators 9 are formed not around a stopper 8 but around an outer circumferential surface of the rod-shaped electrode 3 at intervals of a predetermined distance along the axis line of the rod-shaped electrode 3.

A distal end tip 5 is formed to be opaque with no immobile indicator 7 as described above being provided therearound. As shown in FIG. 11, among the plurality of mobile indicators 9 formed around the rod-shaped electrode 3, mobile indicators 9 that have moved into the distal end tip 5 cannot visually be recognized through the transparent flexible sheath 1.

Consequently, as shown in FIG. 12, the projection length of the rod-shaped electrode 3 can be grasped by checking how many mobile indicators 9 can be observed through the transparent flexible sheath 1 projected from the distal end of the endoscope on the observation window.

FIG. 13 shows a treatment tool for the endoscope in a fourth embodiment according to the present invention. As shown in FIG. 13, the mobile indicator 9 is formed around the outer circumferential surface of the stopper 8 fixed to the base of the rod-shaped electrode 3 in the same manner as the first and second embodiments. However, an immobile indicator 7 is formed around the flexible sheath 1 to be visually recognized directly from the outside of the flexible sheath 1. Such an immobile indicator 7 can be formed by chemical treatment for the flexible sheath 1 or coating around the flexible sheath 1.

In the present embodiment, the immobile indicator 7 is formed in such a position as to overlap the stopper 8 when the projection length of the rod-shaped electrode 3 is zero (namely, when a leading edge of the rod-shaped electrode 3 conforms with a leading edge of the flexible sheath 1).

Therefore, as shown in FIG. 14, when the rod-shaped electrode 3 projects from the distal end of the flexible sheath 1, a positional deviation corresponding to the projection length of the rod-shaped electrode 3 is generated between the mobile indicator 9 and the immobile indicator 7. Hence, as shown in FIG. 15, the projection length of the rod-shaped electrode 3 can easily be recognized as an amount of the positional deviation between the immobile indicator 7 and the mobile indicator 9 that is viewed on the observation window.

FIG. 16 shows a treatment tool for the endoscope in a fifth embodiment according to the present invention. In the fifth embodiment, an immobile indicator 7 similar to the one in the fourth embodiment is formed with a heat shrinkable tube being constricted and fixed around the outer circumferential surface of the flexible sheath 1. Furthermore, the mobile indicator 9 may be formed with the heat shrinkable tube.

It is noted that the present invention is not limited to the aforementioned embodiments. For example, the present invention may be applied to a treatment tool for an endoscope for which a rod-shaped treatment piece that does not allow the high frequency current to flow therethrough is employed instead of the rod-shaped electrode 3.

The present disclosure relates to the subject matter contained in Japanese Patent Application No. P2006-303435 filed on Nov. 09, 2006, which is expressly incorporated herein by reference in its entirety.

What is claimed is:

1. A treatment tool for an endoscope, comprising:
   a flexible sheath configured to be inserted into and ejected from a treatment tool insertion channel of the endoscope, the flexible sheath including a transparent flexible tube provided at least around a distal end of the flexible sheath;
   a rod-shaped treatment piece arranged into the flexible sheath;
   an operation wire arranged inside the flexible sheath to move back and forth along an axis line of the flexible sheath, a distal end of the operation wire being connected with the rod-shaped treatment piece such that the rod-shaped treatment piece is projected back and forth from the distal end of the flexible sheath by operating the operation wire;
   a mobile indicator formed at one of the rod-shaped treatment piece and a portion of the operation wire near the distal end thereof so as to move along with movement of the rod-shaped treatment piece, the mobile indicator being visually recognized through the transparent flexible tube of the flexible sheath from an outside of the flexible sheath;
   a tubular distal end tip fitted into the distal end of the flexible sheath, the distal end tip being configured such that the rod-shaped treatment piece passes therethrough; and
   an immobile indicator formed on an outer circumferential surface of the tubular distal end tip, the immobile indicator being disposed inside the transparent flexible tube of the flexible sheath so as to be visually recognized through the transparent flexible tube from the outside of the flexible sheath.

2. The treatment tool according to claim 1,
   wherein the rod-shaped treatment piece includes a high frequency electrode,
   wherein the flexible sheath is formed from an electrical insulating tube, and
   wherein the operation wire has a function of a conductive wire carrying an electrical current to the high frequency electrode.

3. The treatment tool according to claim 2,
   wherein the operation wire is formed with a stainless steel thin wire being twined or coil-wound around a core wire connected integrally with the rod-shaped treatment piece.

4. The treatment tool according to claim 1, further comprising a braking member configured to give frictional resistance against the movement of the operation wire inside the flexible sheath so as to hold the rod-shaped treatment piece in a state projected from the distal end of the flexible sheath by a desired length.

5. The treatment tool according to claim 4,
   wherein the braking member includes a flexible tube fitted between the operation wire and an inner circumferential surface of the flexible sheath.

6. The treatment tool according to claim 5,
   wherein the braking member is formed from a tetrafluoroethylene resin tube.

7. The treatment tool according to claim 1, further comprising a stopper provided at a base of the rod-shaped treatment piece, the stopper being configured to establish contact with a rear end of the distal end tip so as to regulate a maximum projection length of the rod-shaped treatment piece projecting from the distal end of the flexible sheath.

8. The treatment tool according to claim 7,
   wherein the mobile indicator is formed on an outer circumferential surface of the stopper.

9. The treatment tool according to claim 1,
   wherein the immobile indicator is formed at a rear end on the outer circumferential surface of the distal end tip.

10. The treatment tool according to claim 1,
    wherein the immobile indicator includes a plurality of immobile indicators formed on the outer circumferential surface of the distal end tip along an axis line of the rod-shaped treatment piece at intervals of a predetermined distance.

11. The treatment tool according to claim 1,
    wherein the mobile indicator includes a plurality of mobile indicators formed on the outer circumferential surface of the rod-shaped treatment piece along an axis line of the rod-shaped treatment piece at intervals of a predetermined distance.

12. The treatment tool according to claim 11,
    wherein the distal end tip is formed to be too opaque to visually recognize ones of the mobile indicators shifted thereinto through the transparent portion of the flexible sheath from the outside of the flexible sheath.

13. The treatment tool according to claim 12,
    wherein the distal end tip is formed from electrical insulating polyetheretherketone (PEEK) resin.

14. The treatment tool according to claim 1,
    wherein the flexible sheath includes one of a sheath formed from a transparent flexible tube over an entire length thereof and a sheath formed with a transparent flexible tube being connected with a distal end of an opaque flexible tube.

* * * * *